United States Patent [19]

Oppolzer

[11] 4,179,572

[45] Dec. 18, 1979

[54] TRANS-N-ACYL-N-ALKYL-1-AMINO-1,3-BUTADIENES AND TRANS-N-ACYL-N-ARYL-1-AMINO-1,3,-BUTADIENES

[75] Inventor: Wolfgang Oppolzer, Thônex, Switzerland

[73] Assignee: CHON Corporation, Cambridge, Mass.

[21] Appl. No.: 835,322

[22] Filed: Sep. 21, 1977

Related U.S. Application Data

[62] Division of Ser. No. 647,049, Jan. 7, 1976, Pat. No. 4,065,496.

[51] Int. Cl.$^2$ ............................................. C07C 125/06
[52] U.S. Cl. ...................................... 560/115; 560/132; 560/157
[58] Field of Search ......................... 560/115, 132, 157

[56] References Cited

U.S. PATENT DOCUMENTS

| | | | |
|---|---|---|---|
| 3,764,695 | 10/1973 | Chupp | 560/132 |
| 3,888,888 | 6/1975 | Pallos | 560/157 |
| 3,888,903 | 6/1975 | Chupp | 560/132 |

FOREIGN PATENT DOCUMENTS 540975  9/1955  Belgium .................................... 560/157

OTHER PUBLICATIONS

Oppolzer, Helv. Chim. Acta, 58, pp. 587–595.
"Webster's Third New International Dictionary of the English Language Unabridged", p. 54 (1963).

Primary Examiner—James O. Thomas, Jr.
Assistant Examiner—Michael Shippen
Attorney, Agent, or Firm—Ostrolenk, Faber, Gerb & Soffen

[57] ABSTRACT

Trans-N-acyl-N-alkyl-1-amino-1,3-butadienes are prepared by contacting a conjugated azomethine with a strong base in an inert organic solvent at sub-zero temperature and thereafter acylating the resulting product. The trans-N-acyl-N-alkyl-1-amino-1,3-butadienes are useful as intermediates in the formation of substituted decahydro-quinolines, Pumiliotoxin C, and can also be used as the diene in Diels-Alder reactions or can be copolymerized with vinyl compounds.

8 Claims, No Drawings

TRANS-N-ACYL-N-ALKYL-1-AMINO-1,3-BUTADIENES AND TRANS-N-ACYL-N-ARYL-1-AMINO-1,3,-BUTADIENES

This is a division of application Ser. No. 647,049, filed Jan. 7, 1976 now U.S. Pat. No. 4,065,496.

BACKGROUND OF THE INVENTION

In the course of studies directed toward to the stereo-controlled synthesis of substituted decahydro-quinolines, a method of producing trans-N-acyl-N-alkyl-1-amino-1,3-butadienes was required. However, the readily apparent processes did not yield the desired compounds. Thus U.S. Pat. No. 2,446,172 teaches that N-alkyl-2-aminobutene-3 when heated and then contacted with an acylating agent, possibly in the presence of a catalyst, yields N-alkyl-N-acyl-2-amino-1,3-butadienes. However, direct acylation of N-alkyl-1-imino-2-butenes, which are readily prepared from crotonaldehyde and primary amines, with carboxylic acid anhydrides and/or acid halides in the presence of triethylamine or sodium acetate failed to give the desired dienamides. Under these conditions, the non-conjugated azomethines were effectively converted to N-acyl-enamines.

Accordingly, it is the object of this invention to provide novel trans-N-acyl-N-alkyl-1-amino-1,3-butadiene and a method by which they may be prepared. This and other objects of the invention will become apparent by those skilled in the art from the following detailed description.

SUMMARY OF THE INVENTION

This invention relates to trans-N-acyl-N-alkyl-1-amino-1,3-butadienes and a method by which they may be prepared. More particularly, the invention relates to the preparation of the trans-N-acyl-N-alkyl-1-amino-1,3-butadienes of the formula

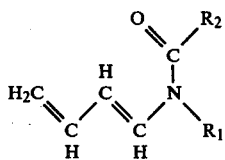

wherein $R_1$ is alkyl, 4-pentenyl, 4-hexenyl, 2-propenyl, aryl or cycloalkyl and $R_2$ is alkyl, 4-pentenyl, 4-hexenyl, 2-propenyl, alkoxy or aryloxy, wherein $R_1$ and $R_2$ each contain 1 to about 8 carbon atoms by contacting a conjugated azomethine with a strong base in an inert organic solvent at sub-zero temperature and thereafter acylating the resulting product by contact with an acyl halide.

DESCRIPTION OF THE PREFERRED EMBODIMENTS

Azomethines, which are also known as aldimines and ketimines, are Schiff base-type compounds. As is well known, they are prepared by reacting a ketone with a primary amine. The azomethine employed in the instant invention is of the formula $CH_3—CH=CH—CH=N—R_1$ and is prepared by reacting crotonaldehyde with a primary amine in accordance with the following equation: $CH_3CH=CH—CHO + R_1NH_2$ $CH_3CH=CHCH=N—R_1$.

In the foregoing formulas, $R_1$ represents an alkyl, aryl or cycloalkyl radical of 1–8 carbon atoms. Thus, $R_1$ can represent $—C_3H_7$, $—C_6H_{13}$, $—CH_2CH=CH_2$, $—CH_2CH_2CH=CH_2$, $—CH_2CH_2CH_2CH=CH_2$, $—CH_2CH_2CH_2CH=CHCH_3$, phenyl, -cyclohexyl, and the like. As is apparent, the corresponding primary amines such as propylamine, hexylamine, aniline, cyclohexylamine, etc., are used to produce the azomethine reactant.

In accordance with the present invention, the azomethines are contacted with a strong base in an inert organic solvent at a sub-zero temperature. The strong bases are generally strong organic bases having a $pK_a$ of 16. Typical examples include sodium hydride, sodium methylsulfinylmethide, sodium hexamethyldisilazane, potassium methylsulfinylmethide, potassium-tert-butoxide and the like. Any inert organic solvent such as toluene, dimethylsulfoxide, dimethoxyethane, tetrahydrofuran and the like can be used.

The concentration of the azomethine in the inert organic solvent or diluent is not critical. Thus, the concentration can range from about 0.001% to 50% although the azomethine is preferably used in diluted form, i.e., at a concentration of about 3% to 10%. The strong base is generally used in an amount of about 1 mol per mol of the azomethine and preferably about 1.1 to 1.5 mol per mol of the azomethine.

The contacting of the conjugated azomethine with the strong base is carried out at sub-zero temperatures, preferably from $-20°$ to $-80°$ C. and most preferably from $-40°$ to $-60°$ C. Without being limited to theory, it is believed that the strong base extracts a proton from the conjugated azomethine to give a delocalized anion

which can then be acylated stereo-selectively at the nitrogen. The observed stereo-selectivity accords with the depicted "W" confirmation of the intermediate anion. It is believed that the sub-zero reaction temperature is necessary for the stability of the delocalized anion. In order to prevent the delocalized anion from undergoing extraneous reactions, it is also preferred to conduct the reaction under an inert atmosphere such as nitrogen, argon or the like. The reaction mixture is also preferably stirred vigorously in order to promote full and efficient contact of the strong base with the azomethine.

The reaction time is not critical and can vary from 1 minute or less to 1 hour or more, as desired. It has been found that reaction times of 0.25 to 0.75 hour is sufficient to provide good product yields.

In the next step of the process, the delocalized anion is acylated stereo-selectively at the nitrogen. This is accomplished by adding a carboxylic acid halide of the formula $R_2CX^O$ to the reaction mixture. Acyl chlorides are preferably used but the other acyl halides such as the bromides and iodides can also be used, if desired. In the foregoing acylating agent formula, X represents the halide and $R_2$ represents an alkyl radical of 1–8 carbon atoms, an aryl radical, an alkoxy radical of 1–8 carbon atoms or an aryloxy radical.

The acyl halide can be used in an amount of 0.5 to 1.5 mols per mol of conjugated azomethine reactant. Preferably, however, it is used in the neighborhood of the stoichiometric amount, i.e., about 1 mol of acyl halide for every mol of conjugated azomethine. The acyl halide is preferably added at the same temperatures used in the production of the delocalized anion. If desired, however, temperatures up to ambient temperature can be employed for the addition of the acyl halide although this is less preferable.

The reaction is allowed to proceed for a period of time which can vary from as little as 1 minute to 10 hours or more. Preferably the acylation reaction is allowed to proceed for 1-6 hours. It is convenient to allow the reaction mixture to warm up to ambient temperature during this time period. Thereafter any excess acylating agent is eliminated by conventional techniques such as by washing the solution several times with water or sodium bicarbonate solution, or aqueous buffer solution pH=7-9. The desired product is then recovered and isolated, e.g., by evaporating the dried solution followed by purification of the residue by chromatography (silica) and/or distillation.

The resulting dienamides are stable and do not decompose to a major extent during chromatography, distillation or during storage for several months in a freezer. The dienamides are useful in the stereo-controlled synthesis of substituted decahydroquinolines and in the production of Pumiliotoxin-C. See Helvetica Chemica Acta, 58, 593 (1975) and Tetrahedron Letters 1975 p. 323. The dieamides are also dienophiles in Diels-Alder reactions (Helvetica Chemica Acta, 58, 590 (1975)) and can be copolymerized with other vinyl compounds in the same manner as the N-alkyl-N-acyl-2-amino-1,3-butadienes, i.e., in the typical vinyl copolymerization process to provide resinous materials which are suitable for making fibers, threads, filaments, films and the like, described in U.S. Pat. No. 2,446,172.

Typical spectral data and product yields of some of the compounds of the present invention are set forth in the following Table. The products were prepared by a procedure designated either A or B in the Table.

In the A procedure, a mixture of 0.66 mol of the primary amine, 0.6 mol of crotonaldehyde, 300 ml of dry benzene and 140 g of molecular sieve was stirred for 6 to 16 hours at 25° C. and then filtered and evaporated to give a crude azomethine as an oily residue. 0.012 mol of the crude azomethine was dissolved in 15 to 60 ml of toluene, cooled to −40° C. under nitrogen and vigorous stirring begun. A 1.67 molar solution of sodium methylsulfinylmethide in dimethylsulfoxide was added to the solution. After 0.5 hours at −40° C., 0.15 mol of acyl chloride was added all at once. The mixture warmed slowly to 0° C. within 3 hours, was kept at room temperature for another 2 hours and was finally washed several times with water. Evaporation of the dried solution and purification by chromatography (SiO$_2$) and/or distillation furnished the dienamides.

The B procedure was the same as the A procedure but instead of the sodium methylsulfinylmethide in DMSO solution, a 2 molar solution of sodium hexamethyldisilazene in toluene was used.

In the C procedure, 0.034 mol of conjugated azomethine in 100 ml of dry dimethoxyethane is added over a period of 15 min. to a well stirred suspension of 3.1 g (0.1 mol) of 80% sodium hydride (in mineral oil) at −60° C., under argon. Thereafter the reaction mixture is left to reach −30° C. and stirred at −30° C. for 1 hour. After addition of 0.12 mol acid chloride the mixture is stirred for 1 hour at −30° C. and for additional 4 hours at 0° C. The excess sodium hydride is decomposed by cautious addition of ice water. After addition of 300 ml pentane the ice cold organic solution is shaken with two portions of 15 ml saturated aqueous sodiumhydrogencarbonate solution, and dried over sodium sulfate. The concentrated solution was purified by filtration through aluminum oxide (neutral, activity II) to furnish the dienamides.

TABLE

| Dienamide | Reaction Conditions | Dist.(bath) °C., Torr | Isolated Yield | $^1$H—NMR (CDCl$_3$) (ppm), H$_A$ | J$_{AB}$(Hz) | IR (film) max$^{(cm-1)}$ | UV(MeOH) max$^{(nm)/log}$ |
|---|---|---|---|---|---|---|---|
| R$_1$=(CH$_2$)$_3$CH=CH$_2$<br>R$_2$=OCH$_3$ | A<br>B<br>C | 100/0.2 | 65%<br>36%<br>89% | 7.06 | 15 | 1720, 1648 | 257.5/4.28 |
| R$_1$=(CH$_2$)CH=CH$_2$<br>R$_2$=OC$_6$H$_5$ | A | 140/0.1 | 61% | not visible | | 1720, 1643 | 208.0/3.99<br>258.0/4.50 |
| R$_1$=(CH$_2$)$_3$CH=CH$_2$<br>R$_2$=CH$_3$ | A | 130/0.1 | 57% | 6.68 | 14,5 | 1676, 1638 | 266.5/4.36 |
| R$_1$=(CH$_2$)$_3$CH=CHCH$_3$<br>R$_2$=OCH$_3$ | B<br>C | 125/0.15 | 48%<br>79% | 7.17 | 15 | 1721, 1648 | 258.0/4.32 |
| R$_1$=(CH$_2$)$_2$CH=CH$_2$<br>R$_2$=OCH$_3$ | A | 125/0.2 | 62% | 7.09 | 14 | 1718, 1645 | 257.0/4.32 |
| R$_1$=cyclohexyl<br>R$_2$=OCH$_3$ | A<br>C | 80/0.1<br>m.p. 38°-40° | 41%<br>82% | 6.79 | 13 | 1720, 1652 | |
| R$_1$=(CH$_2$)$_5$CH$_3$<br>R$_2$=OCH$_3$ | A | 70/0.1 | | 7.31 | 13 | 1730, 1654 | |
| R$_1$=(CH$_2$)$_2$CH$_3$<br>R$_2$=(CH$_2$)$_2$CH=CH$_2$ | A* | 120/0.2 | 60% | 6.90 | 14 | 1675, 1637 | 267.5/4.35 |
| R$_1$=CH$_2$C$_6$H$_5$<br>R$_2$=(CH$_2$)$_2$CH=CH$_2$ | A | — | 0% | | | | |
| R$_1$=C$_6$H$_5$<br>R$_2$=OCH$_3$ | A | 110°/0.1<br>m.p. 56°-57° | 51% | not visible | — | 1726, 1648 | 253.5/4.51 |

*The intermediate n-propyl-1-imino-2-butane was purified by distillation (b.p. 69°-70°/68 Torr) prior to treatment with sodium methylsulfinylmethide at −60° C., followed by addition of allyl acetyl chloride at −60° C.
**This negative result may be attributed to predominant extraction of a benzylic proton in the azomethine (R$_1$ = CH$_2$C$_6$H$_5$) by the base.

Various changes and modifications can be made in the process and products of this invention without departing from the spirit and the scope thereof. The embodiments of the invention disclosed herein were for the purpose of further illustrating the invention but were not intended to limit it.

I claim:

1. A trans-compound of the formula

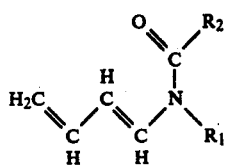

wherein $R_1$ is alkyl, 4-pentenyl, 4-hexenyl, 2-propenyl, or cycloalkyl and $R_2$ is alkoxy or aryloxy, wherein $R_1$ and $R_2$ each contain 1 to about 8 carbon atoms.

2. The trans-compound of claim 1 wherein $R_2$ is methoxy.

3. The trans-compound of claim 2 wherein $R_1$ is —$CH_2CH_2CH_2CH$=$CH_2$.

4. The trans-compound of claim 2 wherein $R_1$ is —$CH_2CH_2CH_2CH$=$CHCH_3$.

5. The trans-compound of claim 2 wherein $R_1$ is —$CH_2CH$=$CH_2$.

6. The trans-compound of claim 2 wherein $R_1$ is cyclohexyl.

7. The trans-compound of claim 2 wherein $R_1$ is hexyl.

8. The trans-compound of claim 1 wherein $R_1$ is —$CH_2CH$=$CH_2$ and $R_2$ is phenoxy.

* * * * *